United States Patent [19]

Weichert

[11] Patent Number: 5,309,216
[45] Date of Patent: May 3, 1994

[54] METHOD OF AND AN APPARATUS FOR DETERMINING PARTICLE SIZE DISTRIBUTIONS BY MEASURING THE SPECTRAL LIGHT EXTINCTION DURING SEDIMENTATION

[76] Inventor: Reiner Weichert, An den Eschenbacher Teichen 21, D-3392 Clausthal-Zellerfeld, Fed. Rep. of Germany

[21] Appl. No.: 894,014

[22] Filed: Jun. 5, 1992

[30] Foreign Application Priority Data

Jun. 7, 1991 [DE] Fed. Rep. of Germany ....... 4118768

[51] Int. Cl.$^5$ ............................................. G01N 15/02
[52] U.S. Cl. ..................................... 356/335; 356/442
[58] Field of Search .................................. 356/335, 442

[56] References Cited

U.S. PATENT DOCUMENTS

| | | | |
|---|---|---|---|
| 4,055,076 | 10/1977 | Tropea | 73/61.4 |
| 4,279,512 | 7/1981 | Tunstall | 356/335 |
| 4,609,991 | 9/1986 | Minton et al. | 364/499 |

FOREIGN PATENT DOCUMENTS

| | | | |
|---|---|---|---|
| 1458870 | 10/1966 | France | |
| 2044490 | 2/1971 | France | G01N 15/00 |
| 1533586 | 11/1978 | United Kingdom | G01N 21/24 |
| 1533587 | 11/1978 | United Kingdom | G01N 21/24 |
| 2046898 | 2/1980 | United Kingdom | G01N 21/27 |

OTHER PUBLICATIONS

Dobbins et al., "Particle Size Measurements Based on Use of Mean Scattering Cross Section", *Journal of the Optical Society of America*, vol. 56, No. 10, (Oct. 1966), pp. 1351-1354.

Weichert, "Determination of Extinction Efficiency and Particle Size Distribution by Photosedimentation using Light of Different Wavelengths", Preprints of Papers to be Presented at the Fourth Particle Size Analysis Conference, Loughborough University of Technology, England, 21-24, pp. 28-35 (1981).

Svarovsky et al., "A New Amalogue Data Analyser for Particle Size Distribution Measurements in a Disc Centrifuge", *Journal of Physics E*, vol. 9, No. 11, pp. 959-962 (1976).

Groves et al., "Development Studies of a Centrifugal Photosedimentometer Using Laser Light", *Powder Technology*, vol. 11, No. 3, pp. 245-255 (1957).

*Primary Examiner*—Richard A. Rosenberger
*Attorney, Agent, or Firm*—Webb, Burden, Ziesenheim & Webb

[57] ABSTRACT

A method of determining particle size distributions in the range of from about 0.03 to 10 $\mu$m by measuring the spectral light extinction during sedimentation of particles suspended in a transparent liquid in a centrifugal field. The light transmissions through the suspension of light of different wavelengths are measured in response to the settling time and the particle size distribution is determined from the light transmissions measured. No knowledge of the optical data of the particles is needed. The integral equation to be solved for that purpose is given. A wide particle size range can be covered precisely within short times of analysis.

11 Claims, 2 Drawing Sheets

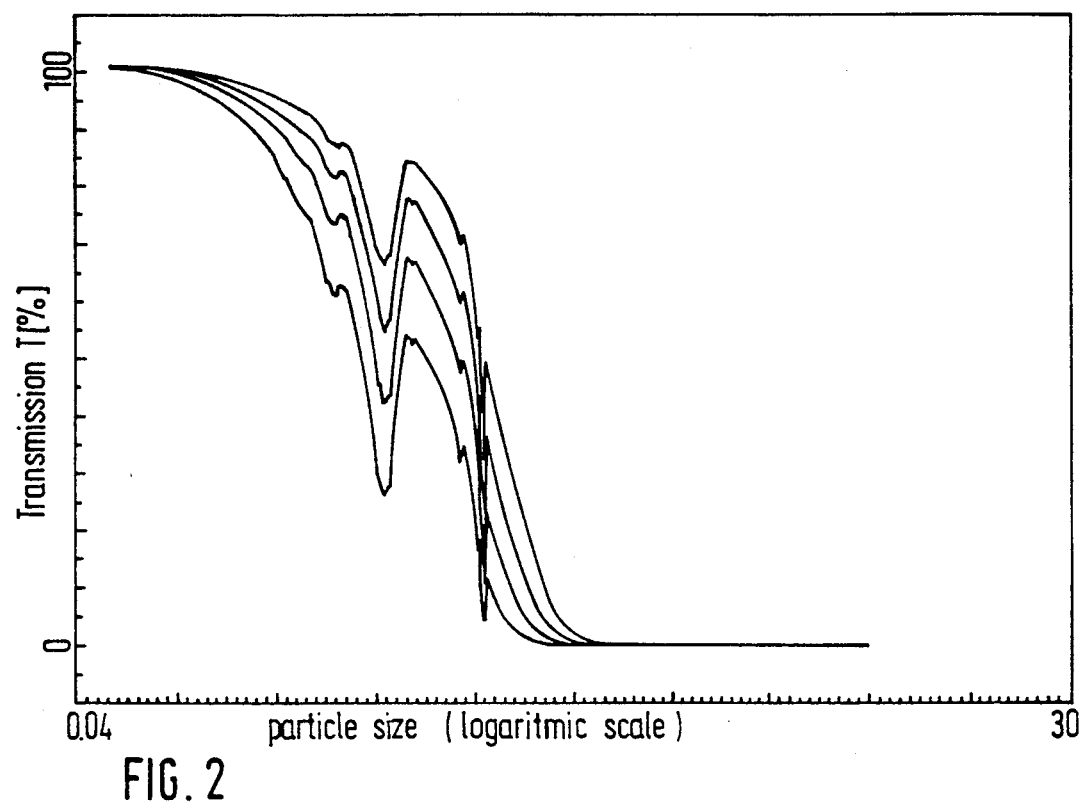
FIG. 2
FIG. 3
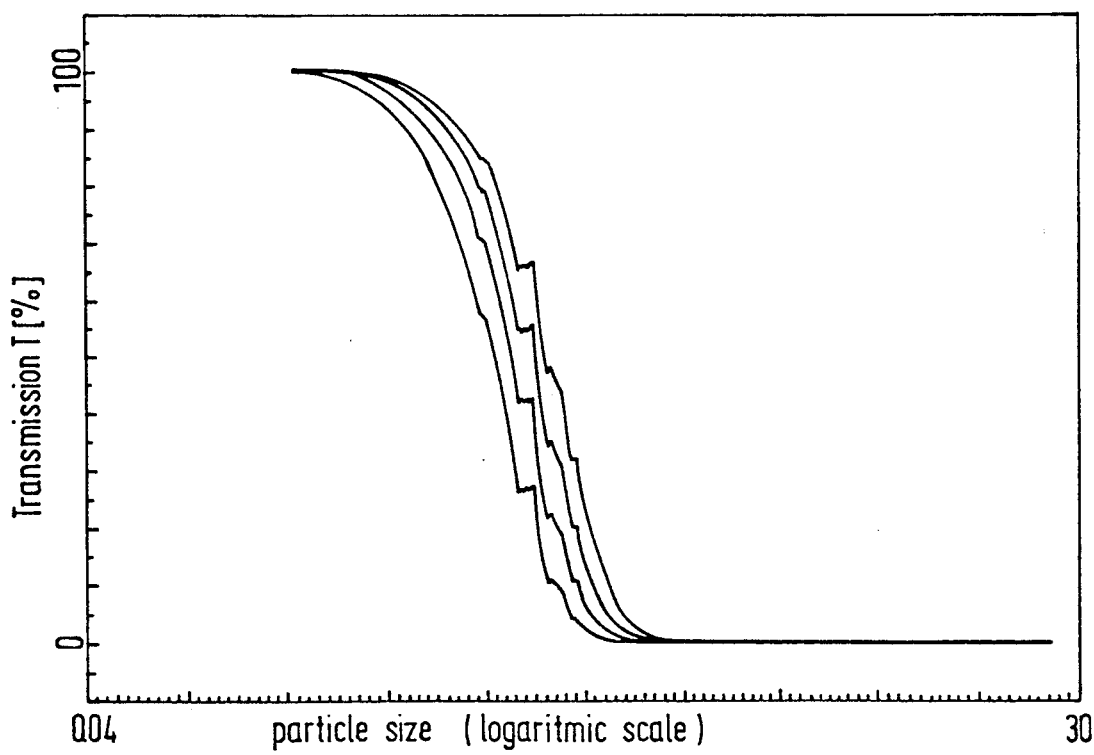

METHOD OF AND AN APPARATUS FOR DETERMINING PARTICLE SIZE DISTRIBUTIONS BY MEASURING THE SPECTRAL LIGHT EXTINCTION DURING SEDIMENTATION

The invention relates to a method and an apparatus for determining particle size distributions, especially in the range of from 0.03 to 10 μm, by measuring the spectral light extinction during the sedimentation of particles which are suspended in a transparent liquid.

BACKGROUND OF THE INVENTION

Methods and apparatus devised to determine particle size distributions by photosedimentation have been known for a long time. With them, the settling velocity (rate) of the particles suspended in the transparent liquid is the measure of the particle size. Sedimentation, in principle, can be effected in the gravitational field or in the centrifugal field. The attenuation of a light beam through the suspension is the measure of quantity, i.e. the amount of particles in a size fraction or class.

Two different sedimentation procedures are currently applied. In the case of the superimposed layer technique (line start technique) at the beginning of the analysis a layer of a concentrated suspension is superimposed over a body of clear liquid. In the case of the suspension technique the suspension is mixed uniformly at the start of the analysis.

With the suspension technique, having made transmission measurements $T(t)$ in a photocentrifuge in response to the settling time (t), the particle size distribution $q_3(x)$ can be calculated by numerical solution of the integral equation $$\ln\left(\frac{1}{T(t)}\right) = c \int_0^{\xi(t)} \frac{K(\pi x/\lambda)}{x} \exp(-2Fx^2\Omega(t)) \, q_3(x) \, dx$$

with $$F = (\rho_s - \rho_f)/18\eta,$$

$$\Omega(t) = \int_0^t (\omega(\tau))^2 \, d\tau, \quad \xi(t) = \sqrt{\ln\left(\frac{R}{r}\right)\frac{1}{F\Omega(t)}}$$

wherein
 $K(\pi x/\lambda)$ is the extinction function dependent on the material,
 $\rho_f$ is the density of the suspension liquid,
 $\eta$ is the viscosity of the suspension liquid,
 $\rho_s$ is the density of the solids particles,
 c is a constant,
 $\omega$ is the number of revolutions of the centrifuge per unit of time,
 r is the inner radius of the cuvette,
 R is the radius at which the transmission measurement is made.

The extinction function K must be known in order to be able to calculate the particle size distribution $q_3(x)$. It belongs to the state of the art to either assume the extinction function K to be constant, or to calculate the extinction function according to the Mie theory. The first choice results in great errors when particles are small as against the light wavelength. The second possibility exists only with spherical particles of which the optical data of the material are known, which is not so in most cases. Only rarely are spherical particles given.

A method is known for photosedimentation under gravitation where the particles travel along straight, parallel paths. It is referred to as spectral photosedimentation with which the extinction function can be determined experimentally during the analysis. To that end, the analysis must be undertaken with light of different wavelengths (R. Weichert, Preprints of papers to be presented at the Fourth Particle Size Analysis Conference, Loughborough University of Technology, England, 21-24 Sep. 1981, pages 28 to 35).

The method of spectral photosedimentation analysis so far could not be applied in a centrifugal field because the particles are not moving along parallel paths, a condition for the spectral photosedimentation in the gravitational field.

SUMMARY OF THE INVENTION

It is the object of the invention to devise a method and an apparatus designed for photosedimentation in a centrifugal field such that the particle size distribution can be determined when the extinction function of the particles to be analyzed is unknown.

Both a method and an apparatus meeting the above object as well as modifications thereof are defined in the appendant claims and become understood by reading the following description.

The sedimentation is effected in a centrifugal field and the light transmissions $T(\lambda,t)$ for light of different wavelengths $\lambda_i (i=1, 2, \ldots)$ are measured in response to settling time (t) and stored in a memory. The particle size distribution $q_3(x)$ is calculated from the light transmissions measured by a method of weighted singular value decomposition.

Starting from the transmission measurements $T(\lambda,t)$ in a photocentrifuge at different light wavelengths $\lambda_i$ in response to the settling time t both the extinction function K and the particle size distribution $q_3(x)$ can be computed by numerical solution of the integral equation $$\ln\left(\frac{1}{T(\lambda,t)}\right) = c \int_0^{\xi(t)} \frac{K(\pi x/\lambda)}{x} \exp(-2Fx^2\Omega(t)) \, q_3(x) \, dx$$

with $$F = (\rho_s - \rho_f)/18\eta,$$

$$\Omega(t) = \int_0^t (\omega(\tau))^2 \, d\tau, \quad \xi(t) = \sqrt{\ln\left(\frac{R}{r}\right)\frac{1}{F\Omega(t)}}$$

wherein
 $K(\pi x/\lambda)$ is the extinction function dependent on the material,
 $\rho_f$ is the density of the suspension liquid,
 $\eta$ is the viscosity of the suspension liquid,
 $\rho_s$ is the density of the solids particles,
 c is a constant,
 $\omega$ is the number of revolutions of the centrifuge per time unit,
 r is the inner radius of the cuvette,
 R is the radius at which the transmission measurement is made.

The numerical solution of the integral equation, done separately for different wavelengths $\lambda_i$ with $i=1, 2, \ldots$ provides $$\Phi(\lambda_i, x) = K(\pi x/\lambda_i) q_3(x).$$

Here the method of weighted singular value decomposition is applied.

$K(\alpha = \pi x/\lambda_i) \cdot q_3(x)$ is calculated by applying $\Phi(\lambda_i, x)$ with $i = 1, 2, \ldots$ $$K(\alpha) = K(\alpha_0) \exp\left(-\int_{\alpha_0}^{\alpha} \frac{\lambda}{\alpha \Phi} \frac{\partial \Phi}{\partial \lambda} d\alpha\right).$$

$K(\alpha_o)$ can be determined from the Fraunhofer approximation since $\alpha_o > 35$.

$\frac{1}{\Phi} \frac{\partial \Phi}{\partial \lambda}$ follows from $\Phi(\lambda_i, x)$.

Thus, $q_3(x)$ is calculated from $K(\alpha)$ and $$\Phi(\lambda_i, x) = K(\pi x/\lambda_i) q_3(x).$$

The following determinations thus can be made $q_3(x)$ from $K(\alpha)$ and $\Phi(\lambda_i, x) = K(\pi x/\lambda_i) q_3(x)$.

The apparatus for carrying out the method comprises cuvettes in which the particles are contained in a liquid suspension. The light transmission measurement $T(\lambda, t)$ is made at different wavelengths, e.g. from three to five wavelengths, especially four wavelengths $\lambda_1, \lambda_2, \lambda_3, \lambda_4$. It is convenient to use cuvettes with two different layer thicknesses above each other, especially 5 mm and 20 mm, to further improve the accuracy of the light transmission measurement. It is advantageous to provide two different sedimentation distances, especially of 2 mm and 20 mm so as to enlarge the range of detectable particle sizes. Measurements at different sedimentation levels, i.e at different radii of the centrifuge, permit the particle size range which can be measured to be extended considerably.

In mathematically evaluating the measurement data obtained, first $$\Phi(\lambda_i, x) = K(\pi x/\lambda_i) q_3(x)$$

is calculated for each wavelength $\lambda_i$, based on the respective light transmission measurement T. Subsequently $K(\alpha)$ is determined according to $$K(\alpha) = K(\alpha_0) \exp\left(-\int_{\alpha_0}^{\alpha} \frac{\lambda}{\alpha \Phi} \frac{\partial \Phi}{\partial \lambda} d\alpha\right)$$

with $K(\alpha_o)$ from the Fraunhofer approximation and $\frac{1}{\Phi} \frac{\partial \Phi}{\partial \lambda}$ $\Phi(\lambda_i, x)$, and finally the following determinations are made $q_3(x)$ from $K(\alpha)$ and $\Phi(\lambda_i, x) = K(\pi x/\lambda_i) q_3(x)$.

The invention makes it possible to determine the photosedimentation of fine particle size distributions of from 0.03 to 10 μm even when the optical data of the material or the extinction factor are unknown. A wide particle size range can be covered. The times for analysis are relatively short. Further operating parameters are an almost constant direction of sedimentation and a narrow light beam through the suspension.

The light source should be one of great brightness because then narrow light beams can be directed through the suspension.

Furthermore, it is convenient to use a centrifuge with controlled rotational speed $$\frac{d\omega}{dt} = f(\omega)$$

in order to be able to determine a wide range of particle sizes and also because then an almost constant sedimentation direction can be obtained.

When using a centrifuge with controlled rotational speed, the number of revolutions is low at the beginning of the analysis. During this time the large particles which settle fast can be detected. Thereafter the rotational speed is increased continuously under computer control, care being taken that no vortex forms in the suspension. Towards the end of the analysis, at high rotational speed, also small particles are determined in the measurements.

The spectral photosedimentation must take place in the centrifugal field, with extinction measurements being made for at least two different light wavelengths.

BRIEF DESCRIPTION OF THE DRAWINGS

The fundamental design of the present invention will now be more particularly described, by way of example, with reference to the accompanying drawings, in which

FIGS. 2 and 3 are diagrams of the light transmissions measured by the photodectors.

DESCRIPTION OF THE PREFERRED EMBODIMENT

Figure 1:
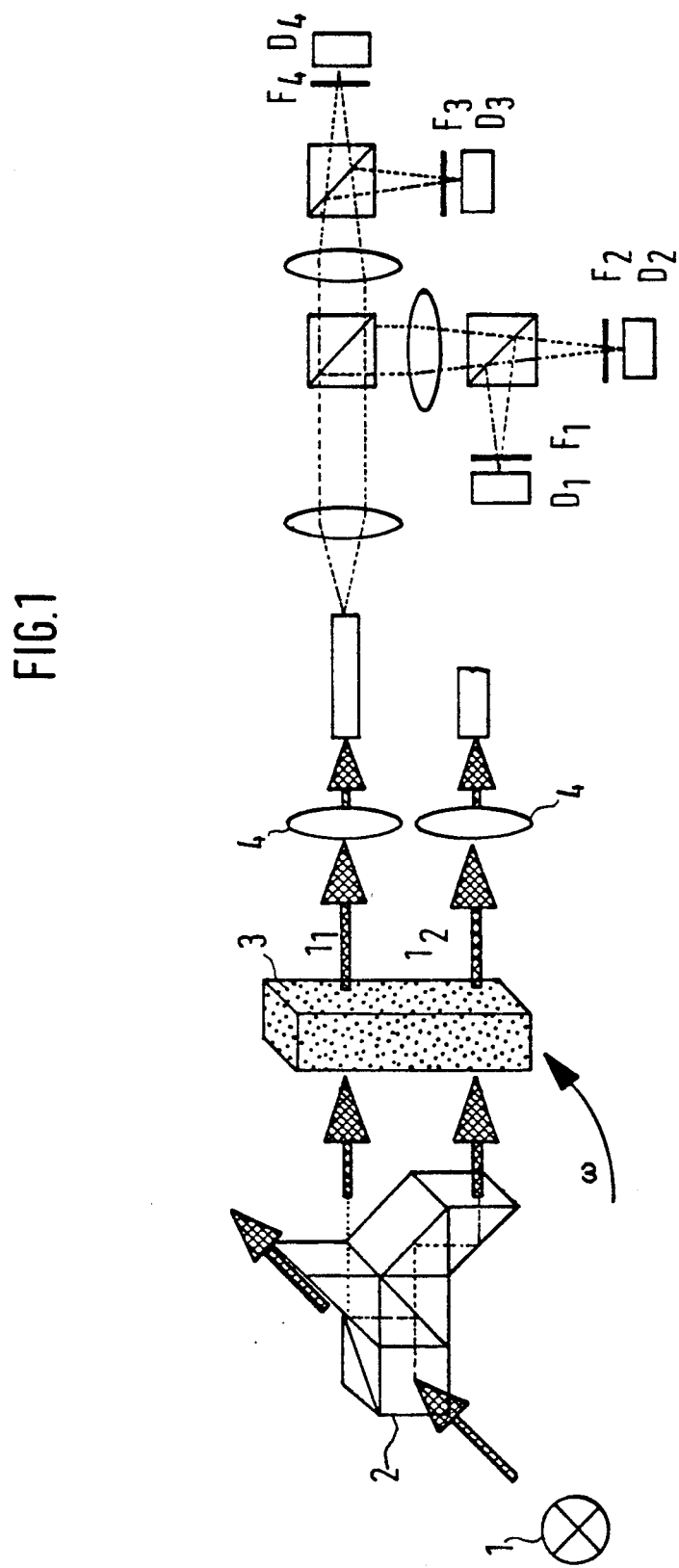
FIG. 1 is a schematic diagram illustrating the arrangement of the illumination means, the cuvettes and the photodetector means useful in understanding the operation of the invention.

A slit is illuminated by the light coming from a light source 1 and is imaged in the middle of a cuvette 3 by means of a lens (not shown). A beam splitter 2 is disposed behind the lens to divide the light beam into a reference beam and a measuring beam. The measuring beam is divided further into an upper partial measuring beam for a measuring level $l_1$ and a lower partial measuring beam for a measuring level $l_2$. The reference beam can be focussed by an additional lens on the aperture of a photoconductor which branches into three individual limbs. The cuvette 3 is followed at both measuring levels by a lens 4 each, with a photoconductor (fiber bundle) of small diameter being arranged in the focal planes thereof and centrally with respect to the opical axis. The light is passed through the two photoconductors for transmission measurement into measuring boxes between which switch-over may be effected with the aid of shutters. Each of the measuring boxes, of which only one is shown, has a reference light photoconductor and a measuring light photoconductor. Beam splitter cubes serve to subject the light coming from the photoconductor to a fourfold division, and four different interference filters $F_1$ to $F_4$ then restrict the light to narrow wavelength ranges ($\lambda_1$ to $\lambda_4$), whereupon the light will reach a respective associated photodetector $D_1$ to $D_4$. The photodetector comprises a photodiode with a built-in hybrid amplifier. A voltage signal proportional to the light intensity is generated. Lenses of equal focal length serve to image the photoconductor on the active detector area of the diode and assure that almost parallel light is present in the area of the beam splitter cubes.

The apparatus further comprises an analyzer means, embodied by a computer, to convert the measured and digitized signals into the particle size distribution looked for, by resorting to the integral equations indicated.

FIGS. 2 and 3 show the transmissions T, measured with the four photodetectors for the four wavelengths $\lambda_1$ to $\lambda_4$ in response to the particle size x (in the logarithmic abscissa scale) for a sedimentation level of 2 mm and 20 mm, respectively, with a cuvette depth of 20 mm in each case, in the direction of the beam.

What is claimed is:

1. A particle size determination method comprising the steps of:

placing a quantity of a transparent liquid containing suspended particles in a device for sedimenting said particles by application of a centrifugal field;

subjecting said transparent liquid and said particles to said centrifugal field and simultaneously exposing said transparent liquid to light of different wave lengths $\lambda_i$ (i=1, 2, ... );

measuring the spectral light extinction by measuring the respective light transmissions (T) through the transparent liquid in response to the settling time (t) and calculating the particle size distribution $q_e(x)$ from the light transmissions measured;

storing the respective light transmissions (T) measurements in a memory; and determining $q_3(x)$ with the following integral equation for the light wave lengths $\lambda_i$ (i=1, 2, ...) used and the stored light transmissions values T $$\ln \frac{1}{(T(\lambda,t))} = c \int_0^{\xi(t)} \frac{K(\pi x/\lambda)}{x} \exp(-2Fx^2 \Omega(t)) \, q_3(x) \, dx$$

with $$F = (P_s - P_f)/18\eta,$$

$$\Omega(t) = \int_0^t (\omega(\tau))^2 \, d\tau, \, \xi(t) = \sqrt{\ln \frac{R}{(r)} \frac{1}{F\Omega(t)}}$$

whereupon $$\frac{1}{\Phi} \frac{\partial \Phi}{\partial \lambda}$$

from $\Phi(\lambda_i, x)$ with i=1, 2, ... is determined from $\Phi(\lambda_i, x) = K(\pi x/\lambda_i) q_3(x)$ $K(\alpha = \pi x/\lambda_i)$ and $q_3(x)$ with i=1, 2, ...

by means of $$K(\alpha) = K(\alpha_o) \exp\left(-\int_{\alpha_0}^{\alpha} \frac{\lambda}{\alpha \Phi} \frac{\partial \Phi}{\partial \lambda} \, d\alpha\right)$$

with $K(\alpha)$ from the Fraunhofer approximation, wherein $K(\pi x/\lambda)$ is the extinction function dependent on the material, $P_f$ is the density of the suspension liquid, $\eta$ is the viscosity of the suspension liquid, $P_s$ is the density of the solids particles, c is a constant, $\omega$ is the number of revolutions of the centrifuge per unit of time, r is the inner radius of the cuvette, and R is the radius at which the transmission measurement is made.

2. The method according to claim 1 wherein said light transmissions (T) measurements are made for at least four wavelengths $\lambda_1$, $\lambda_2$, $\lambda_3$ and $\lambda_4$.

3. The method according to claim 1 wherein said light transmissions (T) measurements are made for at least two layer thicknesses of 5 mm and 20 mm respectively.

4. The method according to claim 1 wherein said light transmissions (T) measurements are made for at least two sedimentation distances of 2 mm and 20 mm respectively.

5. The method according to claim 1 wherein the centrifugal acceleration during the measurements is varied with a view to a large particle size range to be covered and almost constant sedimentation.

6. The method according to claim 5 wherein the measurements first are made at slow rotational speed tuned to the settling rate of the coarse particles, then at continuously increased rotational speed, and finally at high rotational speed to determine small particles.

7. A particle size determination apparatus comprising:

at least one transparent measuring cuvette means for containing a suspension of particles in a transparent liquid;

photocentrifuge means adapted to receive said at least one measuring cuvette means;

an illumination means for transilluminating said cuvette means with bundles of light beams of different wave lengths $\lambda_i$ (i=1, 2, ... );

at least one photodetector means positioned adjacent said cuvette for measuring the respective light transmissions T ($\lambda$,t) during sedimentation; and an analyzer means for computing the particle size distribution $q_3(x)$ from the transmission measurements T, by means of separate numerical solutions of the following integral equation for the light wave lengths $\lambda_i$ (i=1, 2, ... ) used (method of weighted singular value decomposition)

$$\ln \frac{1}{(T(\lambda,t))} = c \int_0^{\xi(t)} \frac{K(\pi x/\lambda)}{x} \exp(-2Fx^2 \Omega(t)) \, q_3(x) \, dx$$

with $$F = (P_s - P_f)/18\eta,$$

-continued $$\Omega(t) = \int_0^t (\omega(\tau))^2 \, d\tau, \; \xi(t) = \sqrt{\ln \frac{R}{(r)} \frac{1}{F\Omega(t)}}$$

whereupon $$\frac{1}{\Phi} \frac{\partial \Phi}{\partial \lambda}$$

from $\Phi(\lambda_i, x)$ with $i = 1, 2, \ldots$ is determined from $$\Phi(\lambda_i, x) = K(\pi x/\lambda_i) q_3(x)$$

$K(\alpha = \pi x/\lambda_i)$ and $q_3(x)$ with $i = 1, 2, \ldots$ by means of $$K(\alpha) = K(\alpha_0) \exp\left(-\int_{\alpha_0}^{\alpha} \frac{\lambda}{\alpha \Phi} \frac{\partial \Phi}{\partial \lambda} \, d\alpha\right)$$

with $K(\alpha)$ from the Fraunhofer approximation, wherein $K(\pi x/\lambda)$ is the extinction function dependent on the material, Pf is the density of the suspension liquid, $\eta$ is the viscosity of the suspension liquid, Ps is the density of the solids particles, c is a constant, $\omega$ is the number of revolutions of the centrifuge per unit of time, r is the inner radius of the cuvette, and R is the radius at which the transmission measurement is made.

8. The apparatus according to claim 7 wherein said illumination means is designed from transilluminating said measurement cuvette with at least three different light wavelengths $\lambda_1$, $\lambda_2$ and $\lambda_3$.

9. The apparatus according to claim 7 wherein said measuring cuvette is designed for two different layer thicknesses of the suspension of a thickness 5 mm and 20 mm respectively.

10. The apparatus according to claim 7 wherein said measuring cuvettes are provided with different sedimentation distances of at least 2 mm and 20 mm.

11. The apparatus according to claim 7 wherein said photocentrifuge means has variable rotational speed.

* * * * *

UNITED STATES PATENT AND TRADEMARK OFFICE
CERTIFICATE OF CORRECTION

PATENT NO. : 5,309,216
DATED : May 3, 1994
INVENTOR(S) : Reiner Weichert

It is certified that error appears in the above-indentified patent and that said Letters Patent is hereby corrected as shown below:

Column 3 Line 60 after the equation insert --from--.

Claim 1 Line 37 Column 5 "$q_e(x)$" should read --$q_3(x)$--.

Claim 1 Line 7 Column 6 "$K(\alpha)$" should read --$K(\alpha_0)$--.

Claim 7 Line 24 Column 7 "$K(\alpha)$" should read --$K(\alpha_0)$--.

Claim 8 Line 14 Column 8 "measurement" should read --measuring--.

Signed and Sealed this

Ninth Day of August, 1994

Attest:

BRUCE LEHMAN

*Attesting Officer*   *Commissioner of Patents and Trademarks*